US008047453B2

(12) United States Patent
Ward et al.

(10) Patent No.: US 8,047,453 B2
(45) Date of Patent: *Nov. 1, 2011

(54) NEUTRAL DISPLACEMENT WICK

(75) Inventors: Bennett C. Ward, Midlothian, VA (US); Wolfgang Broosch, Schwarzenbek (DE); Bernhard Kutscha, Reinbek (DE)

(73) Assignee: Filtrona Porous Technologies Corp., Colonial Heights, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/795,403

(22) Filed: Jun. 7, 2010

(65) Prior Publication Data
US 2010/0243755 A1 Sep. 30, 2010

Related U.S. Application Data

(63) Continuation of application No. 11/765,538, filed on Jun. 20, 2007, now Pat. No. 7,731,102.

(60) Provisional application No. 60/815,822, filed on Jun. 22, 2006.

(51) Int. Cl.
*A61L 9/04* (2006.01)
(52) U.S. Cl. ............ 239/6; 239/44; 239/45; 239/145; 239/326; 222/187; 261/99
(58) Field of Classification Search ............ 239/45, 239/44, 145, 326, 289; 222/187; 261/99
See application file for complete search history.

(56) References Cited

U.S. PATENT DOCUMENTS

| 1,129,897 | A | 3/1915 | Owen, Jr. | 239/45 |
| 2,277,377 | A | 4/1942 | Warner | |
| 4,739,928 | A | 4/1988 | O'Neil | |
| 5,863,196 | A | 1/1999 | Rockwell et al. | 431/325 |
| 6,250,511 | B1 | 6/2001 | Kelly | |
| 6,786,427 | B2 * | 9/2004 | Schram et al. | 239/145 |
| 6,899,280 | B2 | 5/2005 | Kotary et al. | 239/34 |
| 7,055,764 | B1 * | 6/2006 | Martinez et al. | 239/145 |
| 7,731,102 | B2 * | 6/2010 | Ward et al. | 239/45 |
| 2004/0041285 | A1 | 3/2004 | Xiang et al. | 261/99 |
| 2006/0011733 | A1 | 1/2006 | Varanasi et al. | |

FOREIGN PATENT DOCUMENTS

WO WO 2006/004902 A1 1/2006

* cited by examiner

*Primary Examiner* — Dinh Nguyen
(74) *Attorney, Agent, or Firm* — Hunton & Williams LLP

(57) ABSTRACT

Aspects of the invention include an air freshener device that emits fragrance through the evaporation of a fragrance-containing fluid comprising: a container, comprising a particular volume of the fragrance-containing fluid; a wick disposed partially in, and partially out of the fragrance-containing fluid, the wick having an immersion section immersed in the fluid so as to displace a displacement volume of fluid and a non-immersion section extending outward from a surface of the fluid, the immersion and non-immersion section being disposed on opposite lateral ends of the wick; the wick further comprising a displacement portion and a wicking portion, the displacement portion being configured to displace a desired first volume of fluid, the wicking portion being configured to wick a second volume of fluid; the displacement portion and the wicking portion designed to achieve a desired ratio between the displaced first volume of fluid and the wicked second volume of fluid.

20 Claims, 7 Drawing Sheets

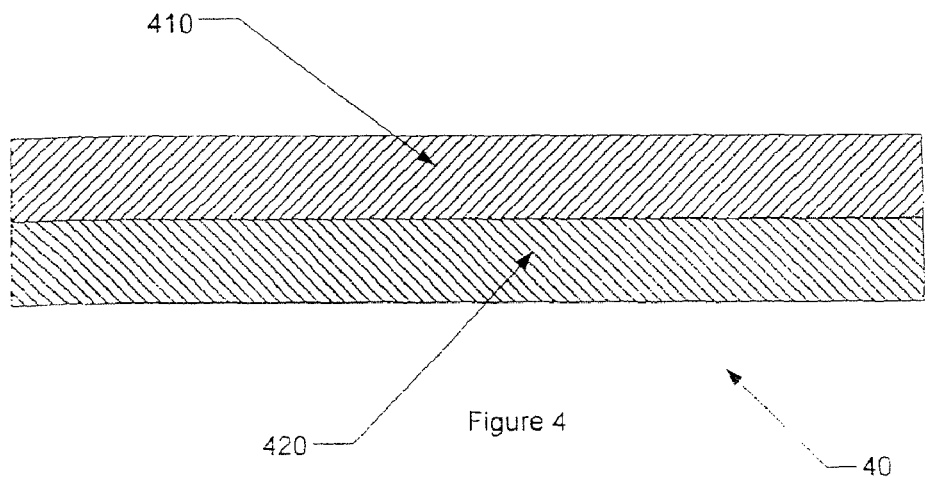
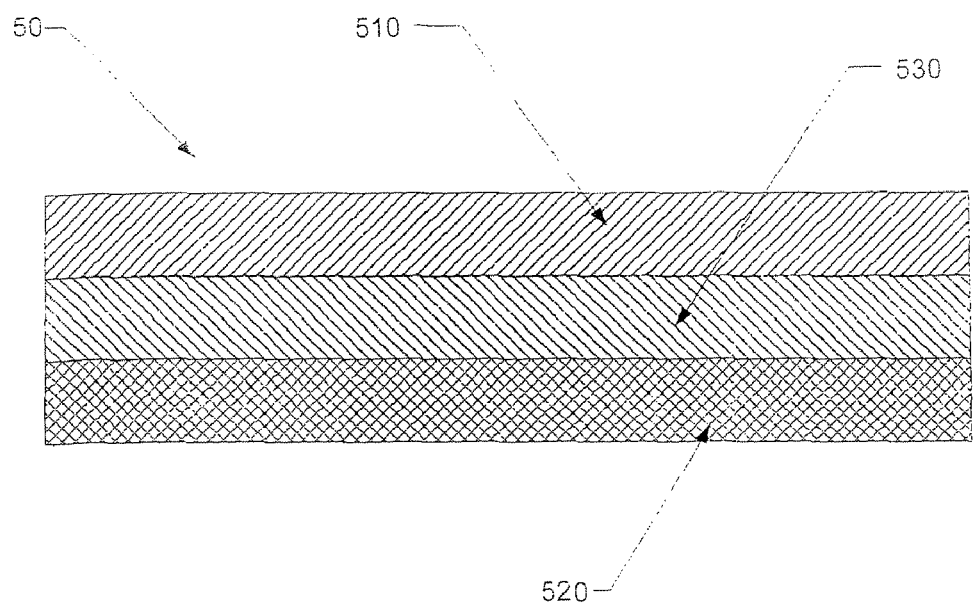

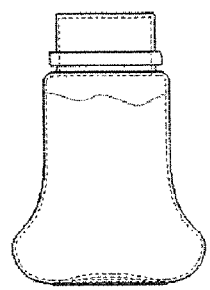
Figure 6
Isotropic Wick Before Introduction to the Bottle
(Prior Art)
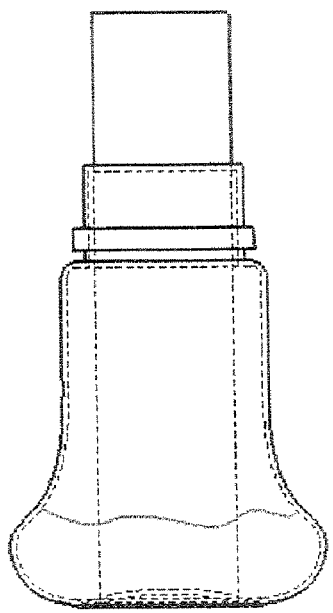
Figure 7
Isotropic Wick Inside of Bottle Showing Relative Drop in Fluid Level
(Prior Art)

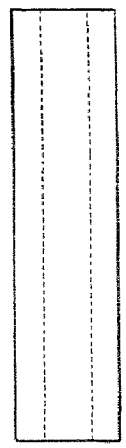
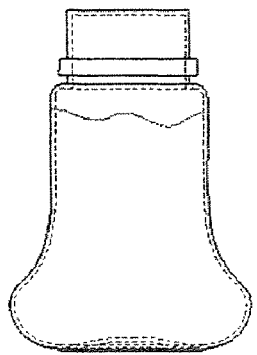
Figure 8
Neutral Displacement Wick Outside of Bottle
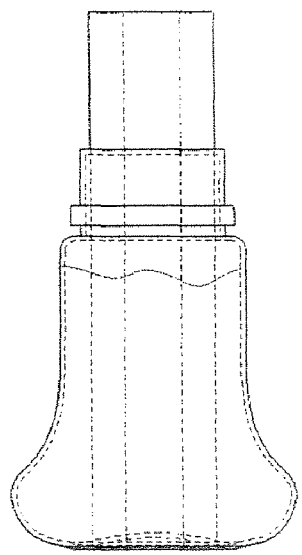
Figure 9
Neutral Displacement Wick Inside of Bottle Wick with "Too Much Core" Inside Bottle
Showing Fluid Overflow

NEUTRAL DISPLACEMENT WICK

This application is a continuation of U.S. application Ser. No. 11/765,538, filed on Jun. 20, 2007, now U.S. Pat. No. 7,731,102, which claims priority to U.S. Provisional Patent Application No. 60/815,822, filed on Jun. 22, 2006 each of which is incorporated herein by reference in their entirety. This application is also related to U.S. application Ser. No. 11/333,499 filed on Jan. 17, 2006, titled "Porous Composite Materials Comprising a Plurality of Bonded Fiber Component Structures," which is also incorporated herein by reference in its entirety.

BACKGROUND OF THE INVENTION

The present invention is generally directed to wicks. In particular, it is directed at wicks where the capillary is formed by fibrous materials. More particularly, the present invention is directed to composite bonded fiber wick structures that displace a specific amount of fluid relative to an amount that is initially absorbed.

It is known in the art to manufacture isotropic wicks for a variety of applications. Such isotropic wicks are generally three-dimensional, porous, bonded fiber elements that may serve to wick a fluid from a first location to a second location. These wicks may be used in diverse applications, such as in air freshener devices, lighters, writing instruments, and for a variety of biological fluids, such as urine and/or blood. Such wicks are disclosed in U.S. patent application Ser. No. 11/333,499, which is herein incorporated by reference in its entirety.

When such bonded fiber wicks are used in air freshener devices, the wick is often immersed in a fluid (typically containing a fragrance), and by capillary force the fluid is drawn into the bulk of the wick. Generally, the end of the wick opposite of the end immersed in the fluid is exposed to air, and the fluid may evaporate from the surface of the wick broadcasting the fragrance into the space around the air freshener device.

However, isotropic wicks used in such air freshener devices and similar applications have several drawbacks. One of the more significant drawbacks is that when an isotropic wick is used to dispense volatile air freshener solutions, the wick generally absorbs an amount of air freshener solution when it is placed in the container. When the wick has a large volume relative to the volume of the container, this may cause the level of liquid in the container to drop as it is absorbed into the wick. In transparent devices sold into the consumer market, such as an air freshener container made of glass or clear plastic, this often creates the negative perception that the consumer is buying a less than full container of air freshener.

Although a smaller diameter wick may at least partially resolve this problem, the surface area of the wick is reduced due to the smaller diameter, and the dissemination of fragrance may be impaired as a result of less surface area of the wick for evaporation.

Accordingly, there is a need for a wick that initially provides a desired amount of fluid displacement while providing sufficient wick surface area for fragrance dissemination. There is also a need for a wick that displaces an amount of fluid approximately equal to the amount of fluid it initially wicks, resulting in a neutral displacement.

SUMMARY OF THE INVENTION

Aspects of the invention include an air freshener device that emits fragrance through the evaporation of a fragrance-containing fluid comprising: a container, comprising a particular volume of the fragrance-containing fluid; a wick disposed partially in, and partially out of the fragrance-containing fluid, the wick having an immersion section immersed in the fluid and an non-immersion section extending outward from a surface of the fluid, the immersion and non-immersion section being disposed on opposite lateral ends of the wick; the wick further comprising a displacement portion and a wicking portion, the displacement portion being configured to displace a desired first volume of fluid, the wicking portion being configured to wick a second volume of fluid; the displacement portion and the wicking portion designed to achieve a desired ratio between the displaced first volume of fluid and the wicked second volume of fluid.

It is to be understood that both the foregoing and the following description are exemplary and explanatory only, and are not restrictive of the invention. The accompanying drawings, which are incorporated herein by reference, and which constitute a part of the specification, illustrate certain embodiments of the invention and, together with the detailed description, serve to explain the principles of the invention.

DESCRIPTION OF THE DRAWINGS

In order to assist in the understanding of the invention, reference will now be made to the appended drawings, in which like reference characters refer to like elements. The drawings are exemplary only, and should not be construed as limiting the invention.

FIGS. 2-5 each depict a cross-sectional view of a multi-component three dimensional bonded fiber wick in accordance with some embodiments of the invention.

FIG. 6 illustrates an isotropic wick as known in the prior art before introduction to the fluid reservoir.

FIG. 7 illustrates an isotropic wick as known in the prior art directly after introduction to the inside of a fluid reservoir.

FIG. 8 illustrates a neutral displacement wick before introduction to the fluid reservoir, in accordance with some embodiments of the present invention.

FIG. 9 illustrates a neutral displacement wick directly after introduction inside of the fluid reservoir, in accordance with some embodiments of the present invention.

DETAILED DESCRIPTION OF THE INVENTION

A neutral displacement wick (NDW) in accordance with some embodiments of the present invention will now be discussed. The advantage of a NDW wick when used in air freshener devices or similar applications is that when the wick is first introduced into the fluid reservoir, it may absorb a desired amount of liquid into the wick relative to the amount it displaces, resulting in the liquid level in the fluid reservoir remaining at or near the level present before the wick was introduced, or at some other desired level. If the wick is capped off or otherwise enclosed to prevent evaporation, the device may be shipped to the consumer who may then have the perception that he or she is buying a full container. When the cap is removed, the large surface area of the wick sheath may allow dissemination of fragrance.

Figure 1:
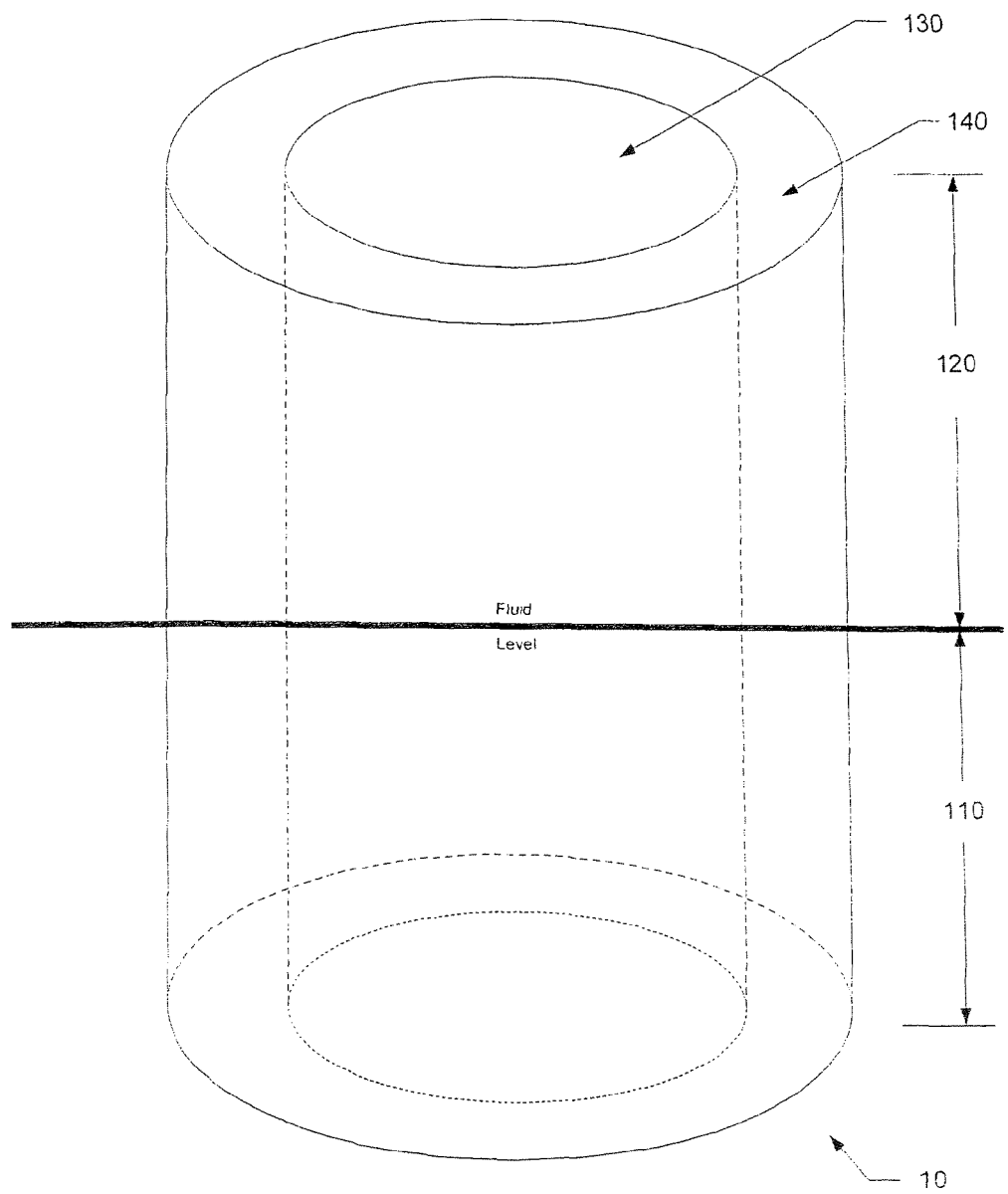
FIG. 1 depicts an isometric view of a multi-component three dimensional bonded fiber wick in accordance with some embodiments of the present invention.

With reference to FIG. 1, a multi-component NDW wick 10 may comprise at least four (4) non-discrete (i.e., overlapping) portions: an immersion section 110, an non-immersion section 120, a displacement portion 130, and a wicking portion 140. The immersion section 110 and the non-immersion section 120 divide the wick laterally, while the displacement portion 130 and wicking portion 140 provide radial divisions in the wick 10. The immersion section 110 is the section of the multi-component wick that is initially in the fluid. The non-immersion section 120 is the section of the multi-component wick that is initially outside of the fluid. The displacement portion 130 may run the entire length of the wick, or may be primarily disposed in the immersion section 110. While the displacement portion 130 may possess some wicking characteristics, its primary purpose is to initially displace a specified amount of fluid. The wicking portion 140 may also run the entire length of the wick, although it is also contemplated to have the majority of the wicking portion 140 in the non-immersion section 120 of the wick. The surface area of the wicking portion 140 in the non-immersion section 120 will determine the dissemination rate of the evaporated fluid.

Figure 2:
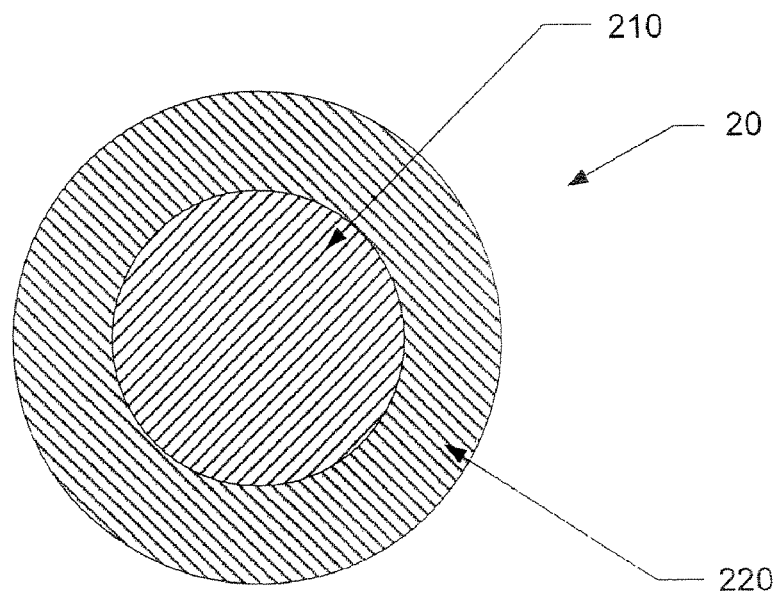
Figure 3:
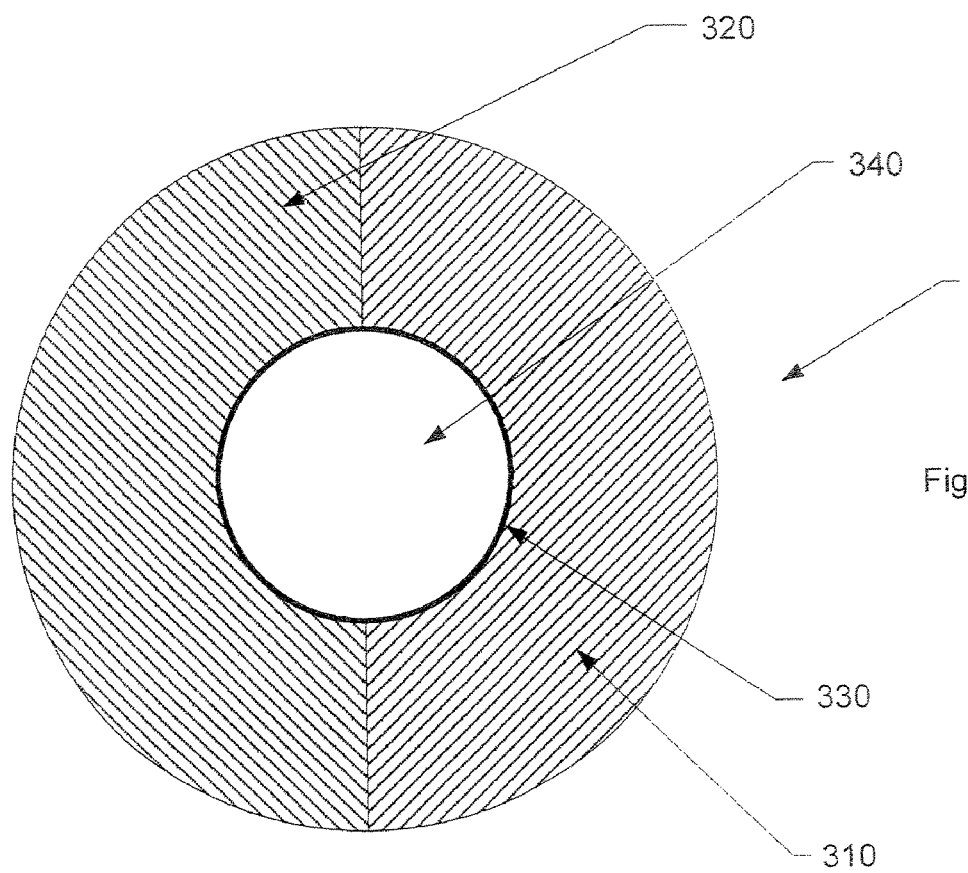

With reference to FIGS. 2-5, various cross-sections of a NDW will now be discussed. In FIG. 2, a NDW 20 may be configured in a cylindrical shape, and may comprise a displacement portion 210 and a wicking portion 220. The displacement portion 210 is shown as being radially-internal to the wicking portion 220. In this manner, the displacement portion 210 may not only be generally hidden, but the wicking portion 220 may be fully exposed to the ambient environment, thereby allowing for optimal evaporation, and thus, fragrance dissemination.

In FIG. 3, a NDW 30 may again be comprised in a cylindrical shape and may comprise a first wicking portion 310, and a second wicking portion 320. The NDW 30 may also comprise an impervious membrane 340 and a void area 350. It is contemplated that the void area 350 may be used similar to the displacement portion in FIGS. 1 and 2 to displace a desired amount of fluid. The first wicking portion 310 may be designed to wick a specific material (e.g., it may be hydrophilic) while the second wicking portion 320 may be designed to wick a different specific material (e.g., it may be oleophilic), providing for multiple scents emitting from the NDW 30. Additionally, the first and second wicking portions 310, 320 may wick the same materials at different rates, or either the first or the second wicking portion 310, 320 may have aromas embedded therein.

In FIG. 4, a NDW 40 may be rectangular in cross-section, and may comprise a displacement portion 410 and a wicking portion 420. Similarly, in FIG. 5, a NDW 50 may comprise at least three (3) portions: a first wicking portion 510, a second wicking portion 520, and a displacement portion 530. Alternatively, the NDW 50 may comprise a wicking portion and a displacement portion separated by an impervious membrane.

Other example cross sections may be a wicking core and a non-wicking sheath, or any other configurations that would be obvious to one skilled in the art.

Many materials may be used in the wicking portion of the NDW wick. Such materials may be self-sustaining porous bonded fiber elements that are well known to be able to be engineered to wick a variety of liquids and act as air freshener wick materials. Examples of such materials may include bonded bicomponent polyolefin sheath fibers, bonded bicomponent polyester sheath fibers, bonded bicomponent nylon sheath fibers and bonded pneumatic nylon and pneumatic cellulose acetate.

Other examples of materials that may be suitable for use in the wicking portion of the NDW wick may include porous, non-bonded, wicking fiber elements, which may be stiffened by adhesives or otherwise made structurally sound to enable consistent wicking behavior. Woven, knitted or non-woven fabrics may be used, as well as natural fibrous or non-fibrous products (such as cotton or wool). In addition, open cell foams may be used (as long as they are of sufficient surface energy to allow wetting and wicking of the target fluid). Additionally, porous plastics, such as self-sustaining porous sintered plastic elements, may be used. Various other materials that provide adequate wicking and evaporation will be readily apparent to one skilled in the art.

In general, the non-wicking portion may be any material as long as it is so configured so that the target fluid will substantially not penetrate this portion and thus be displaced by the non-wicking portion. The non-wicking portion of the NDW wick may be impervious, and may be a closed cell foam material, such as a rod-shaped chemically resistant polyethylene or polyurethane foam, a solid rod, such as a variety of plastic or elastomeric rods, or even rods of wood or metal. The non-wicking portion may also be bonded or non-bonded fiber structures, or natural product structures, with the surface energy being such that the material would not wet out or wick the target fluid, even under elevated pressure conditions that may be experienced in a container.

The wicking portion may be tight up against the non-wicking displacement portion to prevent voids from forming. Unsealed voids are unwanted because upon filling with the fragrant liquid, the volume of the container may appear to be less. The wicking portion and the non-wicking displacement portion may be arranged so as to prevent unwanted delamination or separation of the two portions. For example, the wicking portion and the non-wicking displacement portion may be combined into a single unit by interference fit, or may be adhered together. Such adherence may be the result of fibers of the wicking portion bonding to the non-wicking displacement portion, or may result from the use of adhesives applied to the components.

In general, the wick may be sized to achieve the following objectives:
1. The proper surface area (as determined by the circumference of the wick, the amount of wick exposed in the non-immersion section, and the vapor pressure of the target fluid). A proper surface area may allow a vapor release rate appropriate to the application in question.
2. Appropriate volume of liquid wicked up into the wick by capillary action (determined by the cross sectional area of the wicking portion, plus the capillary draw and porosity of the porous element).
3. The amount of liquid displaced (determined by (2) above plus the displacement of the displacement portion).
4. A desired relationship between the immersion section and the non-immersion section. For example, in some circumstances, it may be desirable to maintain a fluid level at the same height once a wick is inserted. In this situation, the initial volume of the immersion section (comprising the volume of both the displacement portion and the fiber volume of the wicking portion) should be approximately equal to the initial volume of fluid wicked by the wicking portion located in the non-immersion section. In other circumstances, it may be desirable to cause the fluid level to rise or drop once a wick is inserted. In such circumstances, the volume of the immersion section may initially be more or less, respectively, than the volume of fluid initially wicked by the wicking portion in the non-immersion section.

Figure 10:
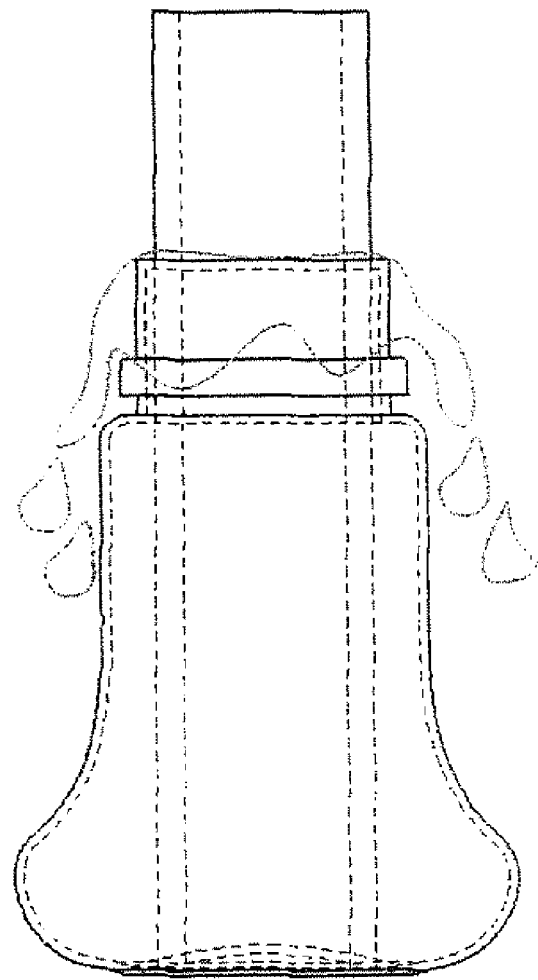
FIG. 10 illustrates an improperly configured wick directly after introduction inside of a fluid reservoir.

The need for proper sizing of the NDW wick may be apparent from FIGS. 6-10. In accordance with some embodiments of the present invention, FIGS. 6-10 illustrate the proper sizing for a NDW where the immersion section displaces an amount of fluid approximately equal to the amount fluid wicked into the wicking portion of the non-immersion section (note that the fluid level remains the same throughout). FIGS. 6 and 7 illustrate the undesirable effect of initial liquid drop in a fluid reservoir when a standard, non-NDW wick is used. It is desirable to properly size or configure an NDW wick to prevent similar fluid drops. FIGS. 8-9 illustrate a properly sized NDW wick that displaces an equal amount of liquid as it initially absorbs, maintaining the initial fluid level at approximately the top of the bottle. FIG. 10 illustrates an improperly sized wick that displaces more fluid than it absorbs, resulting in fluid overflow upon insertion.

The ratio of the volume of liquid displaced by the immersion section (including the displacement portion) to the volume of liquid initially wicked into the wicking portion in the non-immersion section must be designed for each particular application, and must take into account the volume of the container, the size of the NDW and the desired liquid height inside the container before and after the insertion of the NDW. Ratios may range from 0.2 to 4.0. When a particular fluid level prior to NDW insertion is desired to be maintained after NDW insertion, ratios may range from 0.95 to 1.05. Design considerations include, but are not limited to, the desired evaporation rate of the liquid, the surface tension of the liquid that is to be wicked, the density of the wicking portion, the overall dimensions of the wicking portion, and the overall dimensions of the container.

NDW may also be made in many different ways, including bonded fiber processes of many types, non-woven wrapping technologies, textile technologies, and a variety of forming technologies. NDW may be produced by separately manufacturing the porous, wicking portion and the non-wicking portion, and combining the portions into a final unit. As noted above, this combination may utilize an interference fit, may be thermally bonded together as part of the forming process or may utilize additional adhesives.

Alternatively, the wicking portion may be formed integral to the displacement portion. For example, in arrangements such as those depicted in FIGS. 2, and 3 wherein the wicking portion surrounds the displacement portion the wicking portion may be formed around and integral to, the displacement portion, or, in the case of FIG. 3, around a sealed void that provides the desired displacement.

Figure 11:
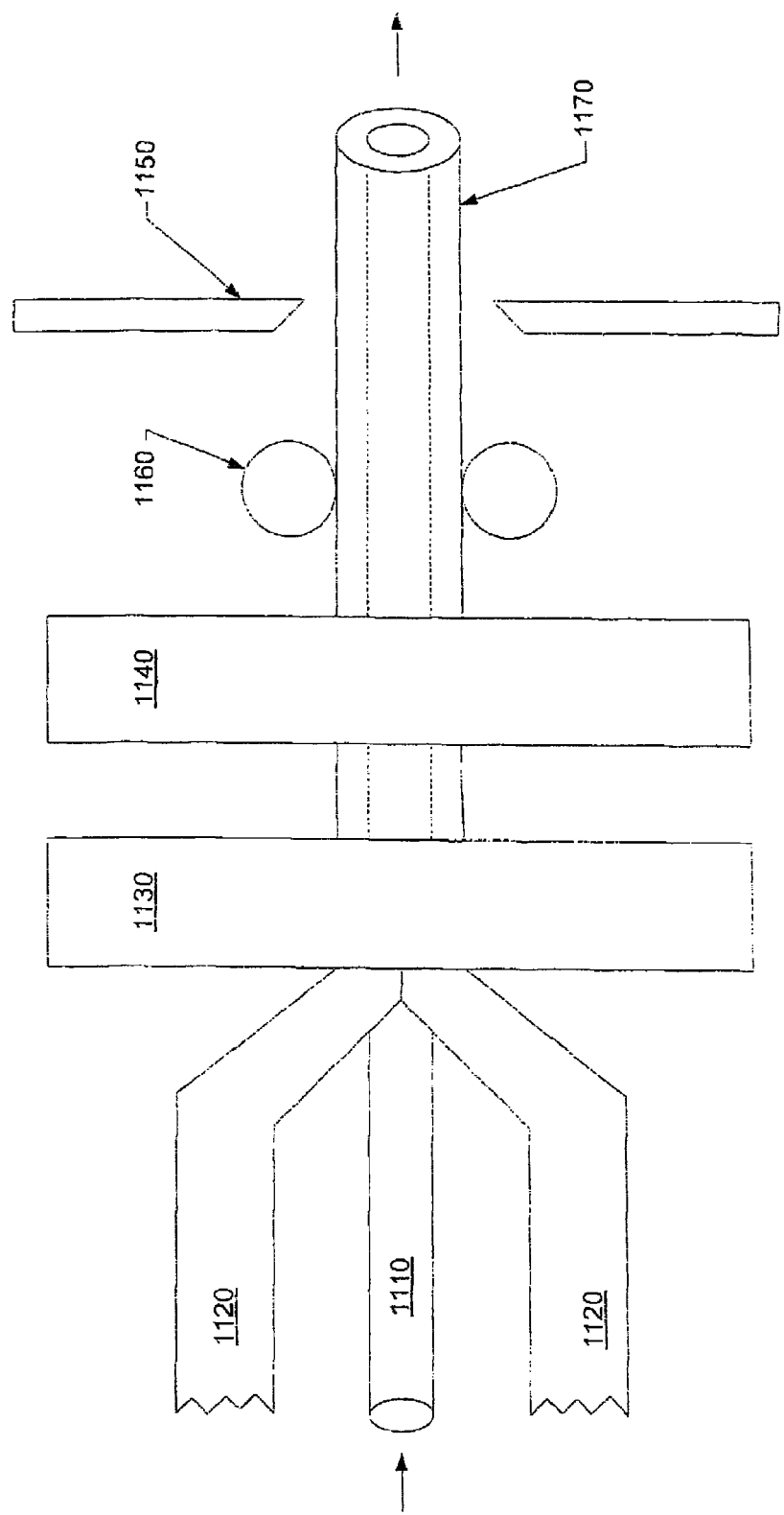
FIG. 11 illustrates a manufacturing process of producing neutral displacement wicks in accordance with some embodiments of the invention.

With reference to FIG. 11, one manner of producing NDW in accordance with some embodiments of the present invention will now be discussed. The displacement portion 1110 may be already formed. The displacement portion 1110 may comprise any material that does not wick or wet out with the intended liquid. For example, the displacement portion 1110 may be a solid, a closed cell foam such as a chemically resistant polyethylene or polyurethane foam. Although the geographic arrangement of the displacement portion 1110 is illustrated in FIG. 11 as being cylindrical, it may take any desired cross-section. The wicking portion 1120 may be formed from a fibrous sheet into a three dimensional, self-sustaining structure around the displacement portion 1110. Sheets or webs of fibrous material 1120 may be fed around the displacement portion 1110 to wrap or encase it. The encased combination of the fibrous material 1120 and the displacement portion 1110 may be fed into a heated die 1130. The die 1130 may be heated by any variety of means (e.g., steam, induction, convection, etc.) and may maintain a temperature above the softening temperature of the fibers of the wicking portion 1120. If the wicking portion 1120 is comprised of bicomponent fibers (e.g., sheath-core or side-by-side bicomponent fibers) the die 1130 may be maintained at a temperature above the softening temperature of the lowest softening (or melting) temperature component. If sheath-core bicomponent fibers are used, the softening temperature of the sheath will be exceeded by the temperature of the die 1130. The heat from the die 1130 may cause the fibers to bond to each other at various points of contact. Upon cooling, the wicking portion may be formed into the desired three dimensional, self-sustaining, porous fiber structure.

The inner dimensions of the die may form the combined wicking portion 1120 and displacement portion 1110 into a desired cross section. Optionally, a cooling die 1140 may be used to quicken the cooling of the heated fibers. Additionally, the cooling die 1140 may provide additional shaping of the cross section of the final product. Upon exit from the heating die 1130 and optionally the cooling die 1140, the NDW 1170 is formed. The combined NDW 1170 may be pulled through the process by element 1160, and may be cut to desired length by element 1150. Although FIG. 11 depicts an NDW 1170 in a cylindrical shape with a circular cross section of both the wicking portion and the displacement portion, it is anticipated that any desired cross section may be obtained.

As noted above, FIG. 11 illustrates a single method for the manufacture of a NDW. Multiple other manufacturing methods may be used to produce, either separately or integrally, the wicking portion and displacement portion of the NDW.

It will be apparent to those skilled in the art that various modifications and variations can be made in the method, manufacture, configuration, and/or use of the present invention without departing from the scope or spirit of the invention.

The invention claimed is:

1. An air freshener device comprising:
   a container having an interior configured for containing a fluid;
   a volume of fragrance-containing fluid disposed within the container, the volume of fragrance-containing fluid has a fluid level relative to the container;
   a wick comprising a wicking portion and a displacement portion, each having an immersion section disposed below the fluid level and a non-immersion section extending above the fluid level, the non-immersion section of the wicking portion containing a wicked volume of the fragrance-containing fluid and the immersion section of the displacement portion displacing a displaced volume of the fragrance-containing fluid, the wicking and displacement portions being configured so that a ratio of the displaced volume to the wicked volume is greater than or equal to 1.0, whereby the fluid level is equal to or higher than an initial fluid level established prior to insertion of the immersion portions of the wick into the fragrance-containing fluid.

2. The air freshener device of claim 1, wherein the ratio of the displaced volume to the wicked volume is 1.0 such that the fluid level is substantially the same as the initial fluid level.

3. The air freshener device of claim 1, wherein the ratio of the displaced volume to the wicked volume is greater than 1.0 such that the fluid level is higher than the initial fluid level.

4. The air freshener device of claim 1, wherein the wicking portion is fibrous.

5. The air freshener device of claim 4, wherein the wicking portion is a bonded fiber structure.

6. The air freshener device of claim 1, wherein the non-immersion section of the wicking portion provides an evaporation surface for the fragrance-containing fluid.

7. The air freshener device of claim 1, wherein the wicking portion comprises a material selected from the group consisting of bonded bicomponent polyolefin sheath fibers, bonded bicomponent polyester sheath fibers, bonded bicomponent nylon sheath fibers, bonded pneumatic nylon, pneumatic cellulose acetate, woven or non-woven fabrics, knitted fabrics, natural or synthetic fibrous or non-fibrous products, cotton, wood, open cell foam, and porous plastics.

8. The air freshener device of claim 1, wherein the displacement portion is comprised of a material selected from the group consisting of closed cell polyethylene foam, closed cell polyurethane foam, solid plastic, metal, and liquid repellant bonded and non-bonded fiber structures.

9. The air freshener device of claim 1, wherein the displacement portion is radially-internal to the wicking portion.

10. The air freshener device of claim 1, wherein the wicking portion is adhered to the displacement portion.

11. The air freshener device of claim 1, wherein the wicking portion and the displacement portion remain in contact due to a mechanical interference fit.

12. The air freshener device of claim 1, wherein the wicking portion comprises a three dimensional, self-sustaining bonded fiber structure and wherein some fibers of the wicking portion are bonded to the displacement portion.

13. The air freshener device of claim 1, further comprising an impervious membrane.

14. The air freshener device of claim 1, wherein the wicking portion is adapted to wick multiple fluidic materials.

15. The air freshener device of claim 1, wherein the wicking portion has aromas embedded therein.

16. A method of assembling an air freshener device comprising:
    providing a container having an interior configured for containing a fluid;
    disposing a volume of fragrance-containing fluid within the container, the volume of fragrance-containing fluid establishing a first fluid level relative to the container;
    providing a wick comprising a wicking portion and a displacement portion; and
    immersing a predetermined portion of the wick into the fragrance-containing fluid so that the wicking portion and the displacement portion each have an immersed section immersed in the fragrance-containing fluid and a non-immersed section extending outward from the fragrance-containing fluid, so that a wicked volume of the fragrance-containing fluid is wicked into the non-immersed section of the wicking portion, and so that the immersed section of the displacement portion displaces a displaced volume of the fragrance-containing fluid, the immersion of the predetermined portion of the wick into the fluid causing the fragrance-containing fluid to establish a second fluid level relative to the container,
    wherein the wicking and displacement portions are configured so that a ratio of the displaced volume to the wicked volume is greater than or equal to 1.0, whereby the second fluid level is equal to or higher than the first fluid level.

17. The method of assembling an air freshener device according to claim 16, wherein the ratio of the displaced volume to the wicked volume is greater than 1.0 such that the second fluid level is higher than the first fluid level.

18. The method of assembling an air freshener device according to claim 16, wherein the wicking portion is a bonded fiber structure.

19. The method of assembling an air freshener device according to claim 16, wherein the non-immersed section of the wicking portion provides an evaporation surface for the fragrance-containing fluid.

20. The method of assembling an air freshener device according to claim 16, wherein the action of providing a wick includes forming the wick so that the wicking portion is integral with the displacement portion.

* * * * *